United States Patent
Park et al.

(10) Patent No.: US 8,325,460 B2
(45) Date of Patent: Dec. 4, 2012

(54) HUMIDITY SENSOR HAVING ANODIC ALUMINUM OXIDE LAYER, AND FABRICATING METHOD THEREOF

(75) Inventors: Hyun-Chul Park, Pohang-si (KR); Hye-Jin Kim, Incheon (KR); Woon-Bong Hwang, Pohang-si (KR); Young-Deuk Kim, Pohang-si (KR); Kun-Hong Lee, Pohang-si (KR)

(73) Assignee: Postech Academy-Industry Foundation, Pohang (KR)

( * ) Notice: Subject to any disclaimer, the term of this patent is extended or adjusted under 35 U.S.C. 154(b) by 511 days.

(21) Appl. No.: 12/617,848

(22) Filed: Nov. 13, 2009

(65) Prior Publication Data

US 2010/0134948 A1    Jun. 3, 2010

(30) Foreign Application Priority Data

Nov. 14, 2008  (KR) .................. 10-2008-0113487

(51) Int. Cl.
*H01G 5/012* (2006.01)
(52) U.S. Cl. .............. 361/286; 361/278; 361/283.1; 361/287; 361/290; 361/292

(58) Field of Classification Search .......... 361/277–278, 361/283.1, 286–287, 290–292; 257/448, 257/431
See application file for complete search history.

(56) References Cited

U.S. PATENT DOCUMENTS 7,872,324 B2 *  1/2011  Kim et al. ............. 257/448
2007/0161313 A1 *  7/2007  Tung .................... 445/24

FOREIGN PATENT DOCUMENTS

| JP | 2001-004579 | 1/2001 |
| JP | 2005-098709 | 4/2005 |
| KR | 10-0568458 | 3/2003 |
| KR | 10-2003-0084279 | 11/2003 |

* cited by examiner

*Primary Examiner* — Nguyen T Ha
(74) *Attorney, Agent, or Firm* — Lexyoume IP Meister, PLLC.

(57) ABSTRACT

Disclosed are a humidity sensor and a fabricating method thereof. The humidity sensor includes a substrate, an anodic aluminum oxide layer formed on the substrate and having a plurality of holes, and electrodes formed on the anodic aluminum oxide layer, in order to improve sensitivity and accuracy of the humidity sensor. Further, the fabricating method of a humidity sensor includes preparing an aluminum substrate, forming an anodic aluminum oxide layer by oxidizing the aluminum substrate, and forming electrodes on the anodic aluminum oxide layer.

16 Claims, 11 Drawing Sheets

HUMIDITY SENSOR HAVING ANODIC ALUMINUM OXIDE LAYER, AND FABRICATING METHOD THEREOF

CROSS-REFERENCE TO RELATED APPLICATION

This application claims priority to and the benefit of Korean Patent Application No. 10-2008-0113487 filed in the Korean Intellectual Property Office on Nov. 14, 2008, the entire contents of which are incorporated herein by reference.

BACKGROUND OF THE INVENTION (a) Field of the Invention

The present invention relates to a humidity sensor and a fabricating method thereof, and more particularly, to a humidity sensor adopting an anodic aluminum oxide layer as a humidity sensing layer, and a fabricating method thereof.

(b) Description of the Related Art

Humidity sensors have been used in various fields, i.e., for cultivation of vegetables in greenhouses, home appliances such as a humidifier, a dryer, and an automatic cooker, humidity control in vehicles or buildings, etc.

In particular, a system-on-a-chip (SOC) realizing a system having various functions on one chip has been actively researched due to nanotechnology development in recent years. An operation frequency is continuously being increased and a minimum line width is continuously being decreased for effective information processing in a highly integrated chip or system. As long as this tendency is continued, parasitic effects, signal delay, and heat related problems are necessarily increased. Among the sub-effects, parasitic capacitances are causes for major losses of a high-frequency system, and are dependent primarily on humidity. Accordingly, sensing the humidity is required to predict and control performance of the high-frequency system.

The humidity sensors are classified as a capacitance type using a polymer, a conductivity type using a ceramic, and a type using an elastic surface wave element in accordance with an operational principle.

The conductivity type or the capacitance type mainly uses a polyimide, etc. as a humidity sensing material, and can measure humidity by using an inter-electrode resistance change or a capacitance change caused by absorption of moisture to the inside of a polymer through proper arrangement of electrodes at both ends or upper and lower sides of the polyimide.

When the moisture is absorbed in a polymer humidity sensing layer, inter-electrode resistance component is varied. At this time, the conductivity type of humidity sensor can measure a change in humidity by detecting the variation of the inter-electrode resistance component.

However, since the polymer humidity sensing layer uses a polymer as the humidity sensing material, the temperature is limited. When the temperature increases to 60° C. or more, the polymer which is an organic material is deformed. The humidity sensing function may be deteriorated by the deformation.

Further, when the polymer is exposed to an environment in which oil or other contaminants are generated for a long time, the surface of the humidity sensing layer is deteriorated or the moisture cannot infiltrate due to clogging of the surface, such that humidity sensing characteristics are deteriorated.

Meanwhile, the capacitance type of humidity sensor detects the change in humidity by measuring the magnitude of a capacitance variation depending on the amount of moisture inputted into the polymer humidity sensing layer. The capacitance type of humidity sensor may provide high precision in comparison with the conductivity type of humidity sensor due to an output characteristic having linearity, but since the capacitance type of humidity sensor uses the polymer, sensitivity and accuracy are deteriorated depending on temperature.

Further, the sensitivity and accuracy of the humidity sensing layer are increased as a surface area becomes larger. However, a process of forming a pattern having a structure of several tens of nanometers in a polymer layer is complicated and the manufacturing cost is increased.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a humidity sensor and a fabricating method thereof having advantages of improving sensitivity and accuracy.

An exemplary embodiment of the present invention provides a humidity sensor that includes a substrate, an anodic aluminum oxide layer formed on the substrate and having a plurality of holes, and electrodes formed on the anodic aluminum oxide layer.

A plurality of holes may be formed in the electrodes, and the holes formed in the electrodes and the holes formed in the anodic aluminum oxide layer may be in communication with each other. Herein, the electrodes may have a thickness of 30 nm to 200 nm.

The electrodes may include a first electrode and a second electrode disposed adjacent to the first electrode. Further, the first and second electrodes may include electrode protrusions, and the electrode protrusions of the first electrode may be fitted between the electrode protrusions of the second electrode.

The electrodes may be formed with one plate shape, the electrodes may be electrically connected with the substrate, and openings opened upward may be formed in the electrodes.

Further, a polymer layer may be formed on the electrodes and the anodic aluminum oxide layer, and a heater may be installed adjacent to the anodic aluminum oxide layer. A power supply and a capacitance meter may be connected to the electrodes.

Another embodiment of the present invention provides a fabricating method of a humidity sensor that includes the steps of preparing an aluminum substrate, forming an anodic aluminum oxide layer by oxidizing the aluminum substrate, and forming electrodes on the anodic aluminum oxide layer.

The fabricating method of a humidity sensor may further include the step of patterning electrodes. The step of patterning the electrodes may include the steps of forming a resist layer on the electrodes, exposing the resist layer, and etching the electrodes.

Further, the step of forming the electrodes may include the step of forming holes in the electrodes. The step of forming the holes may include the step of evaporating a metal constituting the electrodes at a speed of 0.5 Å/s or less.

The step of forming the electrodes may also include the step of evaporating the metal constituting the electrodes in a state in which a shadow mask is installed on the anodic aluminum oxide layer. The fabricating method of a humidity sensor may further include the step of forming a heater to be adjacent to the electrodes.

According to the present invention, a surface area of a humidity sensing layer is maximally extended by utilizing an anodic aluminum oxide layer as the humidity sensing layer to thereby improve sensitivity and accuracy of a humidity sensor.

Further, since air is exposed to the anodic aluminum oxide layer formed below the electrodes by forming the holes in the electrodes, the sensitivity and accuracy of the humidity sensor can be maximized.

In addition, moisture condensed in the holes of the electrodes and the anodic aluminum oxide layer can be easily removed by installing the heater.

Further, the anodic aluminum oxide layer and the electrodes can be prevented from being contaminated by forming the polymer layer on the electrodes and the anodic aluminum oxide layer. Accordingly, it is possible to prevent the lifespan of the humidity sensor from being shortened.

DETAILED DESCRIPTION OF THE EMBODIMENTS

Figure 1:
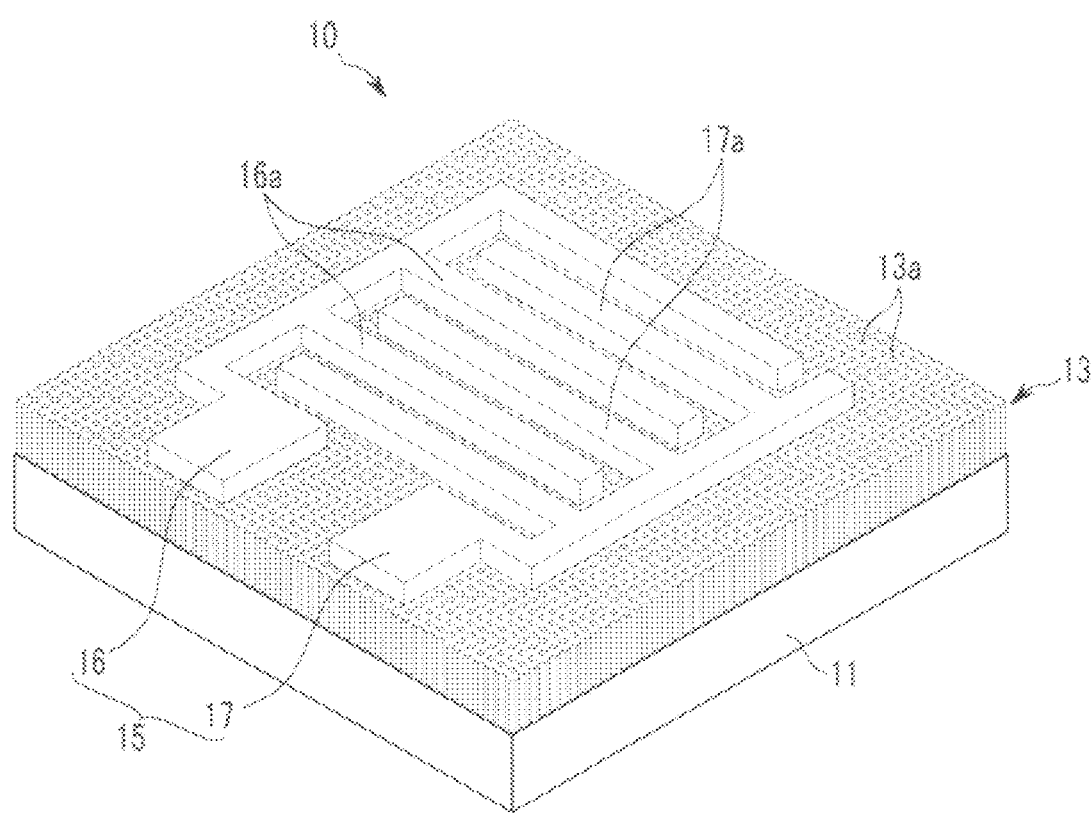
FIG. 1 is a perspective view of a humidity sensor according to a first exemplary embodiment of the present invention.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

FIG. 1 is a perspective view of a humidity sensor according to a first exemplary embodiment of the present invention.

Referring to FIG. 1, a humidity sensor 10 according to the exemplary embodiment includes a substrate 11, an anodic aluminum oxide (AAO) layer 13 formed on the substrate 11, and electrodes 15 formed on the anodic aluminum oxide layer 13.

The substrate 11 is made of aluminum and has a substantially square plate shape.

The anodic aluminum oxide layer 13 is formed by oxidizing the substrate 11. More specifically, the anodic aluminum oxide layer 13 in which a plurality of holes 13a are formed on the surface thereon may be formed by oxidizing aluminum.

At this time, diameters of the holes 13a may be 60 nm or less. When the holes 13a have diameters of 60 nm or less, the holes 13a may be prevented from being damaged by an etching solution.

The electrodes 15 are made of platinum, aluminum, copper, etc., and may be formed by various schemes such as an evaporation method, etc. The electrodes 15 include a first electrode 16 and a second electrode 17 that is disposed adjacent to the first electrode 16. Electrode protrusions 16a protruding toward the second electrode 17 are formed in the first electrode 16 and electrode protrusions 17a protruding toward the first electrode 16 are formed in the second electrode 17.

Further, the electrodes protrusions 16a formed in the first electrode 16 are fitted between the electrode protrusions 17a formed in the second electrode 17, such that the electrode protrusions 16a formed in the first electrode 16 and the electrode protrusions 17a formed in the second electrode 17 engage with each other.

As such, when the electrode protrusions 16a and 17a formed in the electrodes 15 engage with each other, opposed areas between the electrodes 16 and 17 are increased to thereby more sensitively measure a change of capacitance. That is, capacitance between the first electrode 16 and the second electrode 17 is changed depending on a change in humidity of the anodic aluminum oxide layer 13 serving as a humidity sensing layer. Therefore, it is possible to easily measure the humidity through the change of the capacitance. That is, when the humidity is high, a dielectric constant increases, such that the capacitance is changed. The humidity is measured through the change of the capacitance depending on such a relationship between the humidity and the dielectric constant.

A power supply (not shown) and a capacitance meter (not shown) are connected to the first electrode 16 and the second electrode 17 in order to measure the change of the capacitance. A power supply for an apparatus mounted with the humidity sensor 10 may be used as the power supply or an additional power supply may be installed and used as the power supply. Various types of generally used capacitance meters may be adopted as the capacitance meter.

When the humidity is measured through the change of the capacitance, it is possible to measure the humidity more precisely than with a structure measuring the humidity through a change of resistance. This reason is that the capacitance is linearly changed depending on the change of the humidity.

In the exemplary embodiment, although the humidity is measured through the change of capacitance, the present invention is not limited thereto, and the humidity may be measured through the change of resistance, etc.

As described in the exemplary embodiment, when the anodic aluminum oxide layer 13 is used as the humidity sensing layer, surface area to volume of the humidity sensing layer is maximized, such that sensitivity and stability of the humidity sensor are improved.

Figure 2:
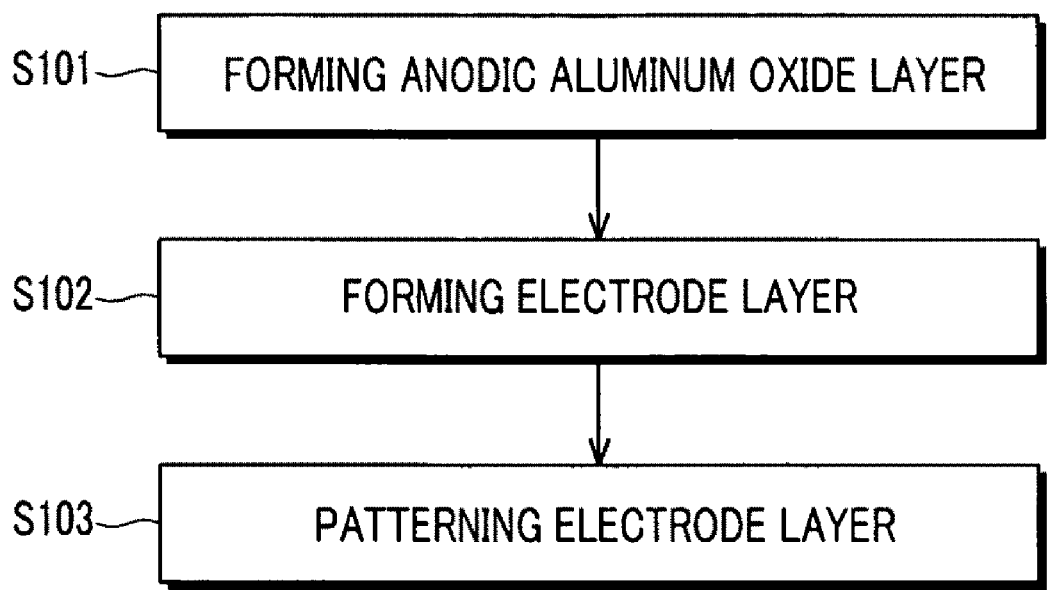
FIG. 2 is a flowchart of a fabricating method of a humidity sensor according to a first exemplary embodiment of the present invention.

FIG. 2 is a flowchart of a fabricating method of a humidity sensor according to a first exemplary embodiment of the present invention. Referring to FIG. 2, the fabricating method of a humidity sensor according to the exemplary embodiment includes the steps of forming an anodic aluminum oxide layer by preparing a substrate and oxidizing the substrate (S101), forming electrode layer on the anodic aluminum oxide layer (S102), and patterning the electrode layer (S103).

In the step of forming the anodic aluminum oxide layer (S101), the anodic aluminum oxide layer is formed by oxidizing an aluminum substrate. After the aluminum substrate 11 is connected to an anode and is immersed in an electrolytic solution, the aluminum substrate 11 is electrolyzed to thereby form an oxide film having adhesion with a metal by oxygen generated from the anode. This is referred to as an anode oxidation treatment. When the substrate 11 is electrically conducted as the anode in electrolytic solutions such as sulfuric acid, a phosphoric acid-chromic acid aqueous solution, etc., in accordance with the anode oxidation treatment, hydrogen gas is generated from a cathode and an oxygen gas is generated from the anode. At this time, the oxygen gas reacts with the aluminum substrate 11 to form the anodic aluminum oxide layer 13 having the adhesion with the metal on the surface of the substrate.

Figure 3A:
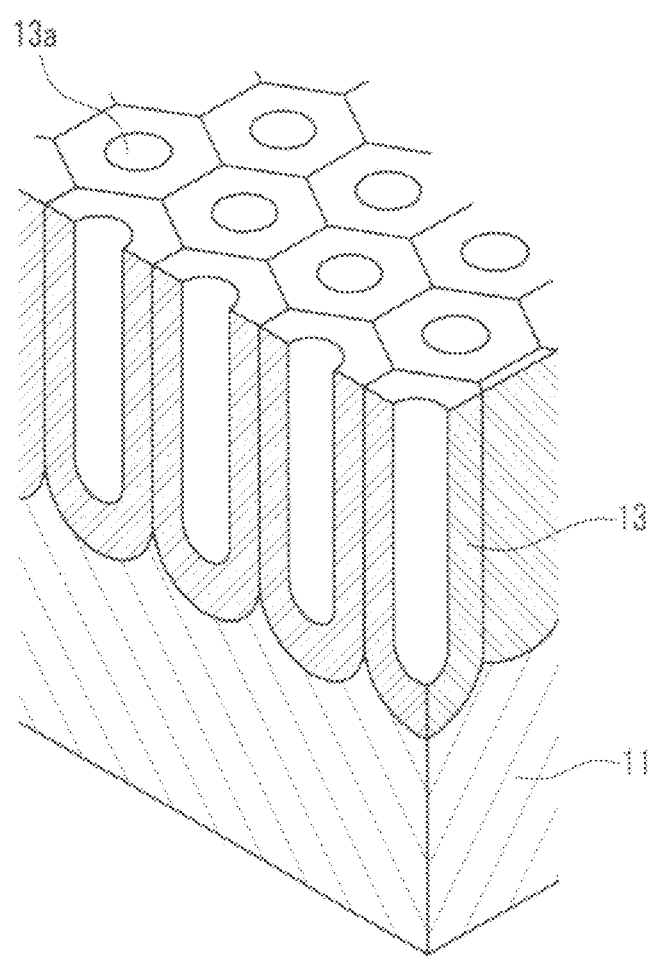
FIG. 3A is a cross-sectional perspective view of an anodic aluminum oxide layer according to a first exemplary embodiment of the present invention.
Figure 3B:
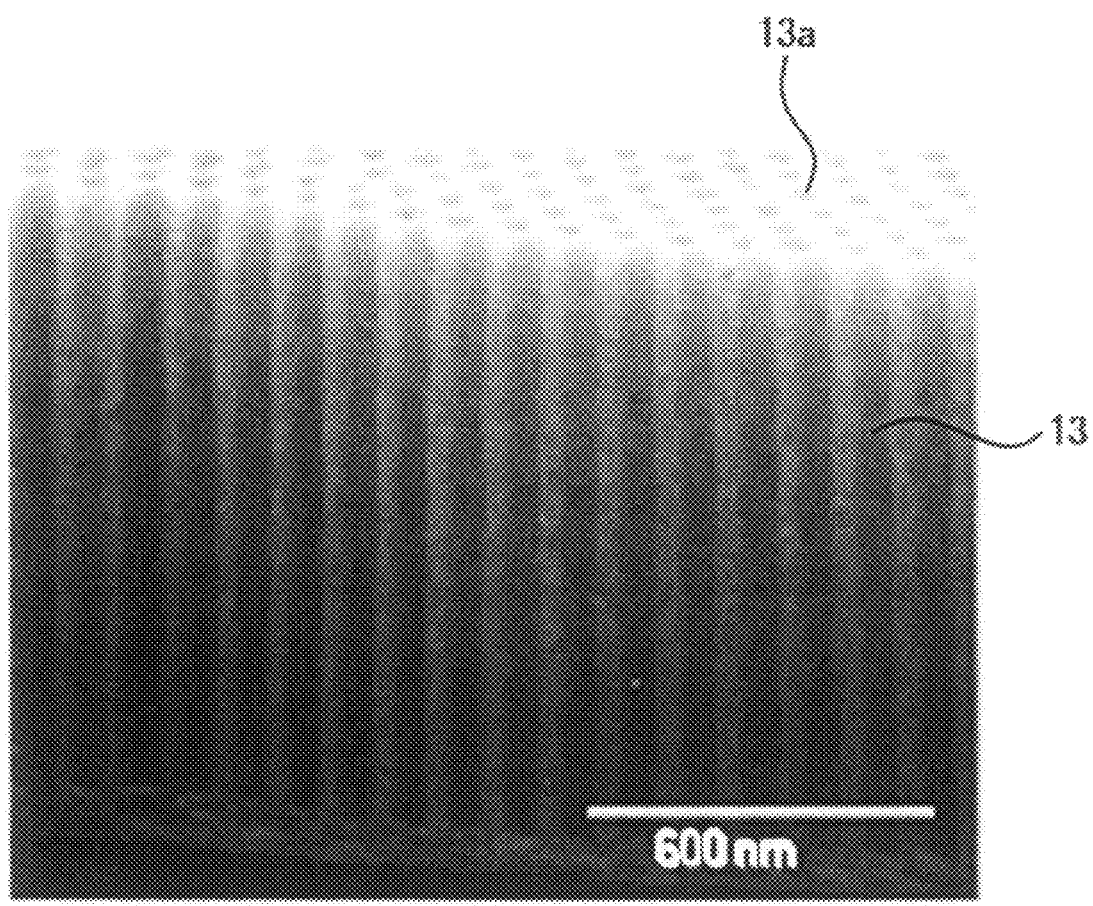
FIG. 3B is a photograph of an anodic aluminum oxide layer according to a first exemplary embodiment of the present invention.

FIG. 3A is an enlarged cross-sectional perspective view of the substrate and the anodic aluminum oxide layer formed on the substrate, and FIG. 3B is a photograph of the anodic aluminum oxide layer formed on the substrate.

As shown in FIGS. 3A and 3B, holes 13a are formed in the anodic aluminum oxide layer 13 by a predetermined rule. The surface area of the anodic aluminum oxide layer 13 is increased as large as surface areas of the holes 13a.

When the anodic aluminum oxide layer 13 is formed, the electrodes are formed on the anodic aluminum oxide layer 13 (S102). The electrodes 15 are made of metals such as platinum, copper, aluminum, etc., and may be formed by various schemes such as an evaporation method, etc. The electrodes 15 are evaporated on the anode aluminum oxide layer in a desired thickness by means of equipment such as an E-beam evaporator or a thermal evaporator.

When the electrodes 15 are formed, the electrode protrusions 16a and 17a are formed by patterning the electrode layer (S103). The electrode layer may be patterned by a lithography process or a shadow mask process. First, the lithography process will be described.

After the electrode layer is evaporated, a hexa methyl disilazane (HMDS) layer and a resist layer are formed. The HMDS layer serves to facilitate bonding of the resist layer and a porous layer. The HMDS layer and the resist layer may be formed by spin coating or by evaporation.

When the resist layer is formed, the resist layer is cured by a soft baking process. Thereafter, in a state in which a photomask is installed on the resist layer, ultraviolet rays are irradiated to the resist layer installed with the photomask, which is exposed.

When the exposure is completed, a photoresist layer is developed and the soft baking process is performed. Thereafter, an electrode pattern is formed by etching the electrode layer.

Next, the shadow mask process will be described. A shadow mask is a stainless plate in which holes are formed in accordance with a desired pattern shape.

After the shadow mask is attached to the anodic aluminum oxide layer, the metal is evaporated at a low speed and the shadow mask is removed. Therefore, the metal is evaporated at a part of the shadow mask where the holes are formed, such that an electrode pattern is formed. Line widths of the electrodes must not be too small or complicated in order to pattern the electrodes 15 by means of the shadow mask.

Figure 4:
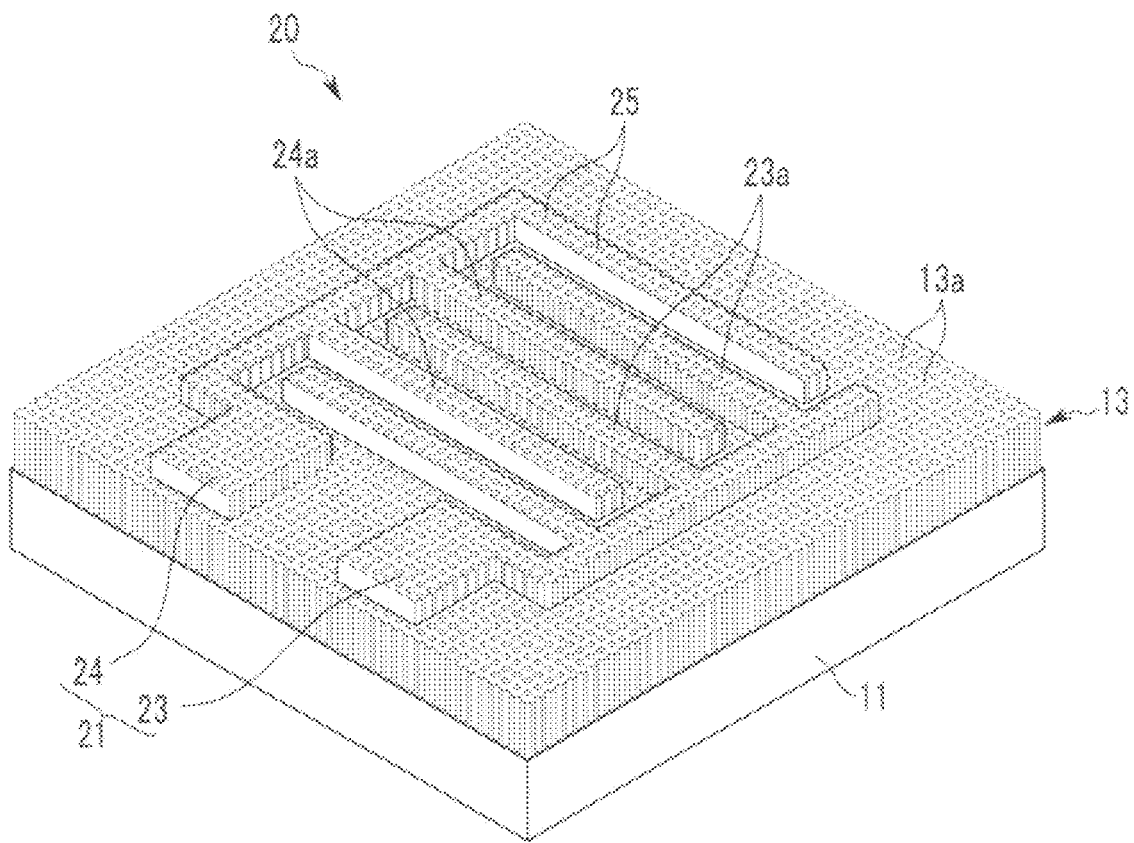
FIG. 4 is a perspective view of a humidity sensor according to a second exemplary embodiment of the present invention.

FIG. 4 is a perspective view of a humidity sensor according to a second exemplary embodiment of the present invention.

Referring to FIG. 4, a humidity sensor 20 according to the exemplary embodiment includes a substrate 11, an anodic aluminum oxide layer 13 formed on the substrate 11, and electrodes 21 formed on the anodic aluminum oxide layer 13.

The humidity sensor 20 according to the exemplary embodiment has the same structure as the humidity sensor according to the first exemplary embodiment except for the electrodes 21. Therefore, the same components will not be repetitively described.

The electrodes 21 include a first electrode 23 and a second electrode 24 that is disposed adjacent to the first electrode 23. Electrode protrusions 23a protruding toward the second electrode 24 are formed in the first electrode 23, and electrode protrusions 24a protruding toward the first electrode 23 are formed in the second electrode 24.

Further, the electrodes protrusions 23a formed in the first electrode 23 are fitted between the electrode protrusions 24a formed in the second electrode 24, such that the electrode protrusions 23a formed in the first electrode 23 and the electrode protrusions 24a formed in the second electrode 24 engage with each other.

Further, a plurality of holes 25 are formed in the first electrode 23 and the second electrode 24. The holes 25 are formed above the holes 13a formed on the anodic aluminum oxide layer 13.

As such, the metal is evaporated at a low speed in order to form the holes 25 in the electrodes 21. The metal is preferably evaporated at a speed of 1 Å/s to 0.2 Å/s. When the evaporation speed of the metal is greater than 1 Å/s, the metal blocks the holes 13a, and when the evaporation speed of the metal is less than 0.2 Å/s, the metal is not normally evaporated.

When the metal is evaporated at a low speed, the metal is not laminated in the holes 13a formed in the anodic aluminum oxide layer 13 in the course of the evaporation and the metal is laminated only in a part where the holes 13a are not formed, such that the holes 25 may be formed in the electrodes 21. As a result, the holes 13a formed in the anodic aluminum oxide layer 13 and the holes 25 formed in the electrodes 21 are in communication with each other.

When the holes 25 are formed in the electrodes 21 as well as the anodic aluminum oxide layer 13, the anodic aluminum oxide layer 13 is further exposed, such that absorption and desorption of moisture are facilitated, thereby further improving sensitivity and accuracy. Further, when the holes 13a of the anodic aluminum oxide layer 13 and the holes 25 of the electrodes 21 are in communication with each other, the moisture may be inputted into the holes 13a of the anodic aluminum oxide layer 13 through the holes 25 of the electrodes 21. As a result, the sensitivity and the accuracy are further improved.

Figure 5:
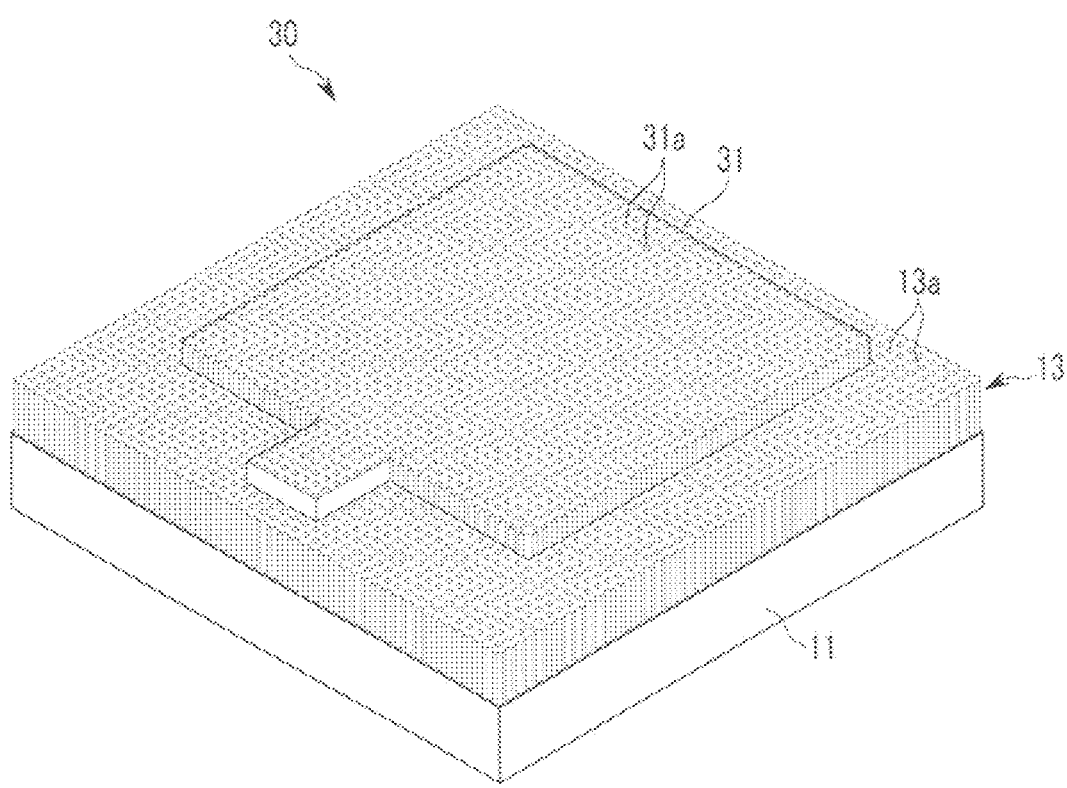
FIG. 5 is a perspective view of a humidity sensor according to a third exemplary embodiment of the present invention.

FIG. 5 is a perspective view of a humidity sensor according to a third exemplary embodiment of the present invention.

Referring to FIG. 5, a humidity sensor 30 according to the exemplary embodiment includes a substrate 11, an anodic aluminum oxide (AAO) layer 13 formed on the substrate 11, and electrodes 31 formed on the anodic aluminum oxide layer 13.

The substrate 11 is made of aluminum. The anodic aluminum oxide layer 13 is formed by oxidizing the substrate 11. Meanwhile, the electrodes 31 are made of metals such as platinum, aluminum, etc. A plurality of holes 31a are formed on the surface of the electrodes 31, like the electrodes according to the second exemplary embodiment.

The electrodes 31 according to the exemplary embodiment have a flat plate shape. One electrode 31 is formed in the anodic aluminum oxide layer 13. The electrode 31 is electrically connected with the substrate 11 made of aluminum, such that the substrate 11 serves as another electrode. At this time, a power supply (not shown) and a capacitance meter (not shown) may be connected to the substrate 11 and the electrode 31.

As such, the electrode 31 and the substrate 11 are installed parallel to each other, and a change of humidity is detected by measuring a change of capacitance that varies depending on a change of internal humidity. In the exemplary embodiment, although the substrate serves as the electrode, the present invention is not limited thereto and an additional electrode may be further formed.

According to the exemplary embodiment, a capacitance type of humidity sensor measuring the humidity by using the change of the capacitance may be provided. The capacitance type of humidity sensor has higher measurement precision than a resistance type of humidity sensor due to an output characteristic having comparative linearity.

Figure 6:
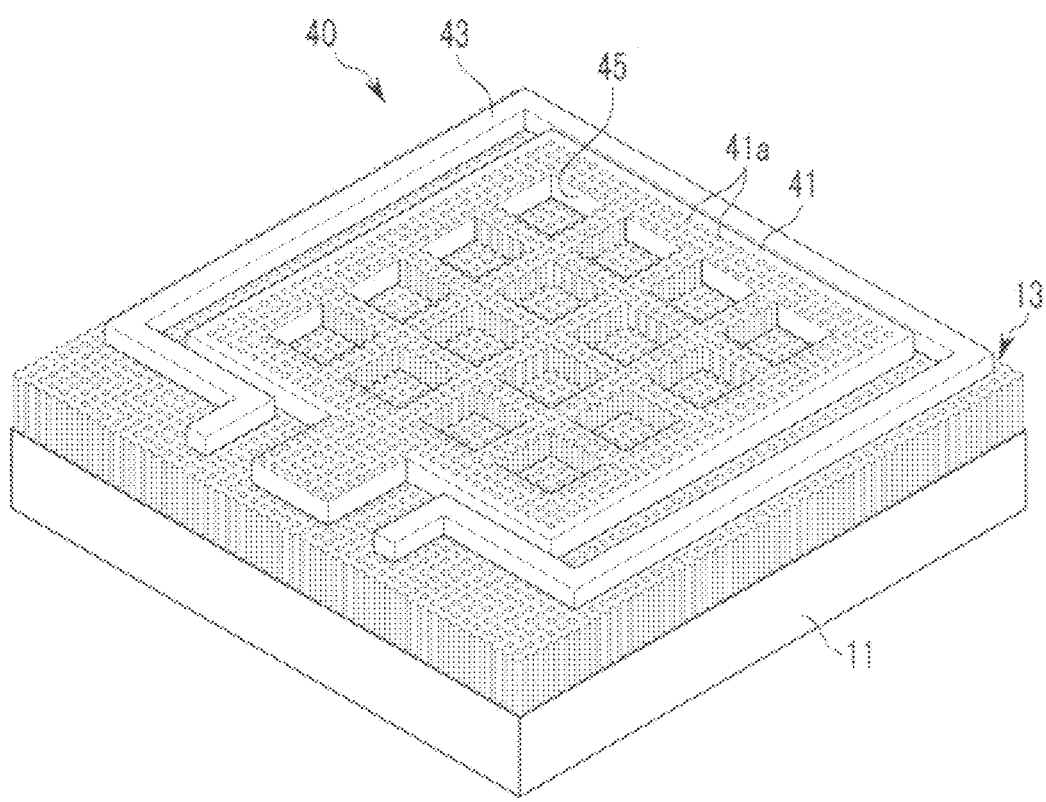
FIG. 6 is a perspective view of a humidity sensor according to a fourth exemplary embodiment of the present invention.

FIG. 6 is a perspective view of a humidity sensor according to a modified example of a fourth exemplary embodiment.

Referring to FIG. 6, a humidity sensor 40 according to the exemplary embodiment includes a substrate 11, an anodic aluminum oxide (AAO) layer 13 formed on the substrate 11, and an electrode 41 formed on the anodic aluminum oxide layer 13.

A plurality of openings 45 are formed in the electrode 41. The openings 45 are larger than holes 41a. The openings 45 have a structure that is opened upward. Upper parts of the openings 45 are opened and lower parts of the openings 45 are linked to the anodic aluminum oxide layer 13. As a result, an area of the anodic aluminum oxide layer 13 that is in contact with external air is increased, thereby maintaining high sensitivity and accuracy.

Further, a heater 43 is installed around the electrode 41. The heater 43 is composed of a heating wire generating heat by using electricity. The heater 43 is separated from the electrode 41 and is formed in a circumferential direction of the electrode 41.

In a state in which humidity is high, vapor is condensed in holes 13a and 41a of the anodic aluminum oxide layer 13 and the electrode 41, and the vapor is not well desorbed and thus blocks the holes 13a and 41a. In this case, sensitivity and stability of a humidity sensing layer consisting of the anodic aluminum oxide layer 13 are deteriorated. In order to solve the above-mentioned problems, the heater 43 is installed. The heater 43 serves to compensate for a temperature as well as evaporate moisture condensed in the holes 13a and 41a.

Figure 7:
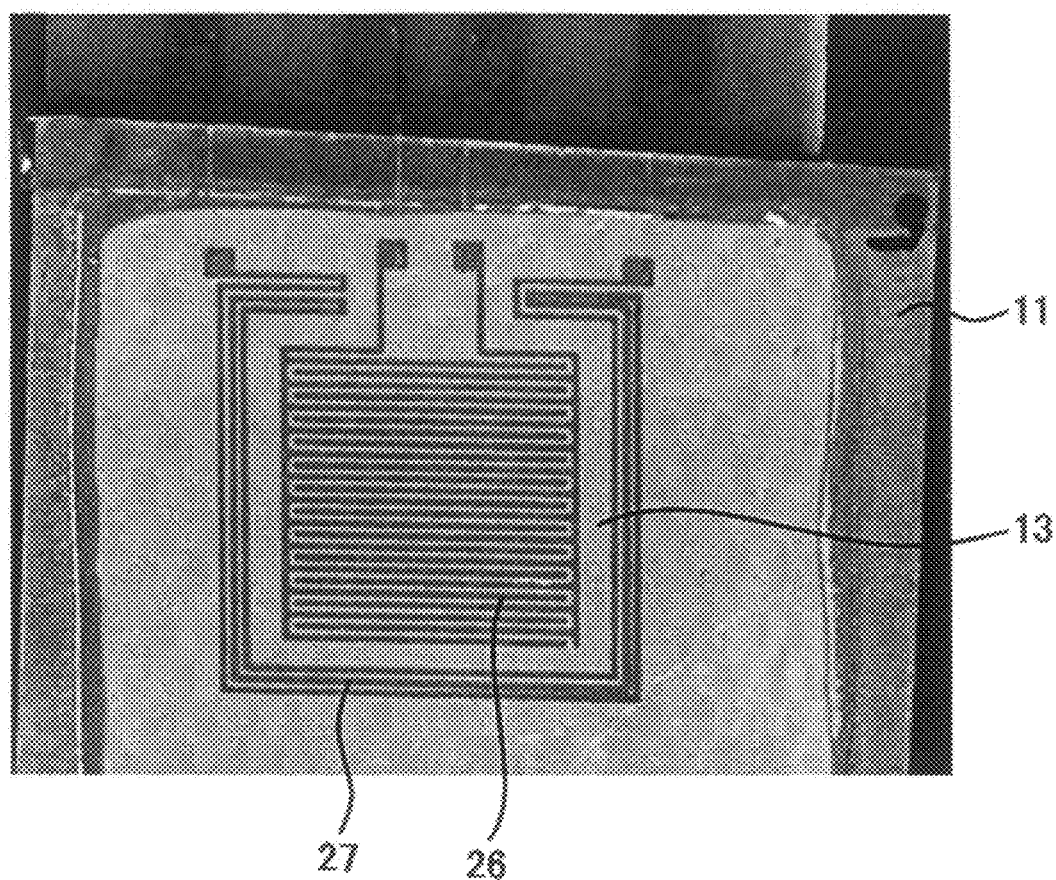
FIG. 7 is a photograph of a humidity sensor according to a fifth exemplary embodiment of the present invention.

FIG. 7 is a photograph of a humidity sensor fabricated according to a fifth exemplary embodiment of the present invention.

Referring to FIG. 7, the humidity sensor according to the exemplary embodiment of the present invention includes an aluminum substrate 11, an anodic aluminum oxide layer 13 formed on the substrate 11, an electrode 26 formed on the anodic aluminum oxide layer 13, and a heater 27 installed around the electrode 26.

Figure 8A:
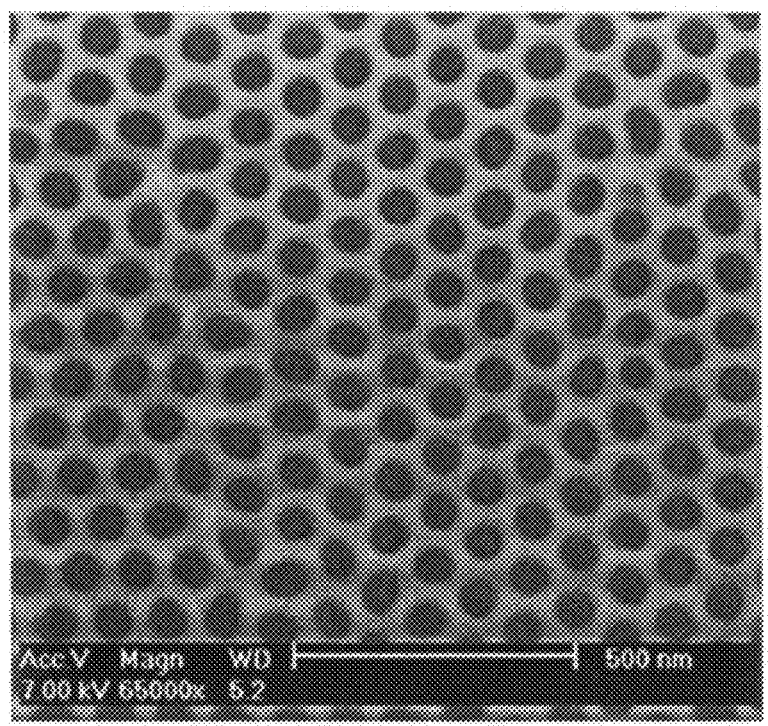
FIG. 8A is a photograph of an anodic aluminum oxide layer of a humidity sensor according to a fifth exemplary embodiment of the present invention.

The anodic aluminum oxide layer 13 is formed by oxidizing the aluminum substrate 11. As shown in FIG. 8A, a plurality of holes are formed on the surface of the anodic aluminum oxide layer 13.

Figure 8B:
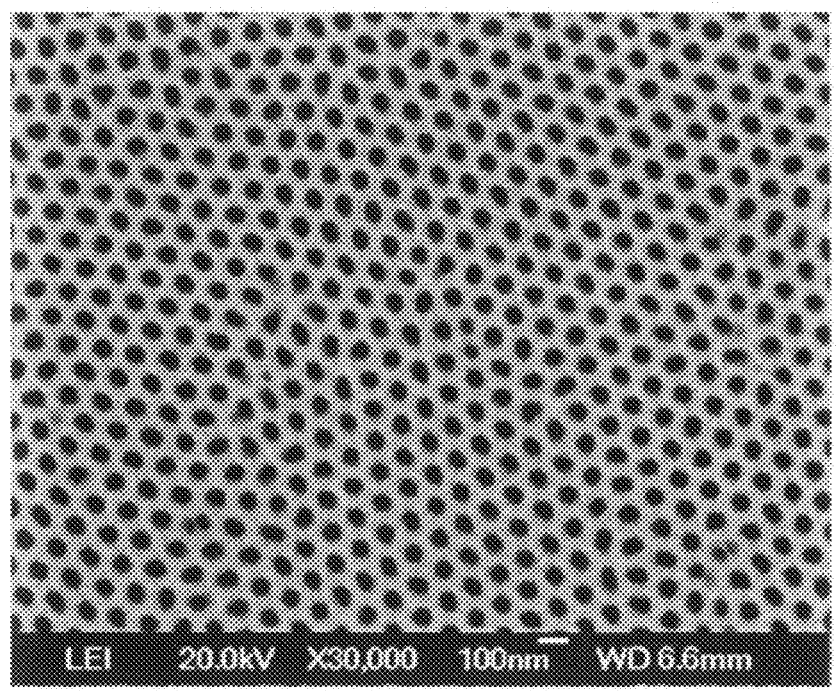
FIG. 8B is a photograph of an electrode of a humidity sensor according to a fifth exemplary embodiment of the present invention.

In the exemplary embodiment, the electrode 26 is divided into two. Each of the two electrodes has a protrusion. Neighboring electrode protrusions fit with each other. Further, as shown in FIG. 8B, the plurality of holes are formed on the surface of the electrode 26 while the electrode 26 is formed.

In the exemplary embodiment, diameters of the holes are 80 nm and a thickness of the anodic aluminum oxide layer 13 is 30 μm. Further, the electrode has a thickness of 150 nm. The electrode is formed by evaporating platinum at a speed of 0.5 Å/s or less so that the holes are not blocked. The electrode is fabricated at a thickness of 30 nm to 200 nm. When the thickness of the electrode is greater than 200 nm, the holes are blocked, and when the thickness of the electrode is less than 30 nm, capacitance is not well measured and sensitivity is remarkably deteriorated.

The heater 27 is installed on the anodic aluminum oxide layer. The heater 27 is separated from the electrode and is formed in a circumferential direction of the electrode while surrounding the electrode. Therefore, the heater 27 efficiently transmits heat to the electrode 26 and the anodic aluminum oxide layer 13 to easily evaporate moisture condensed in the holes of the electrode 25 and the anodic aluminum oxide layer 13.

Figure 9:
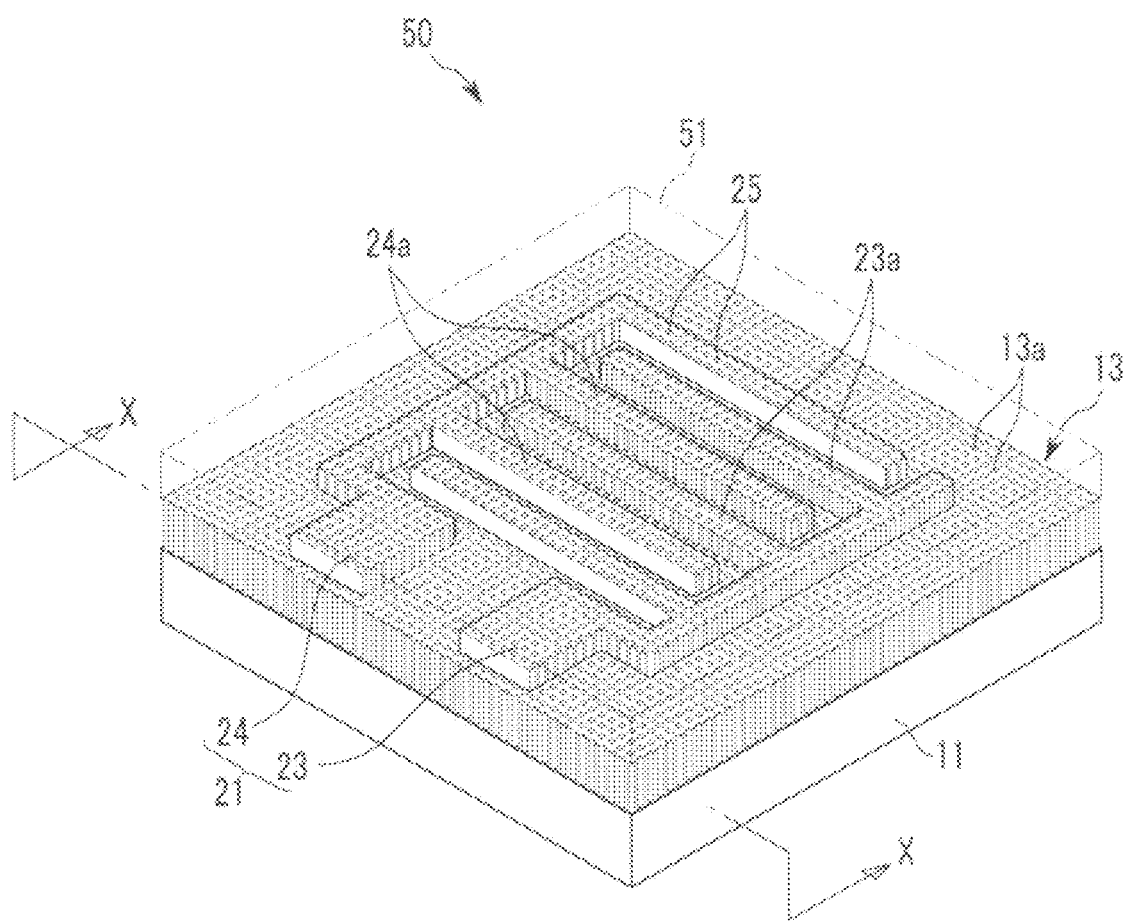
FIG. 9 is a perspective view of a humidity sensor according to a sixth exemplary embodiment of the present invention.
Figure 10:
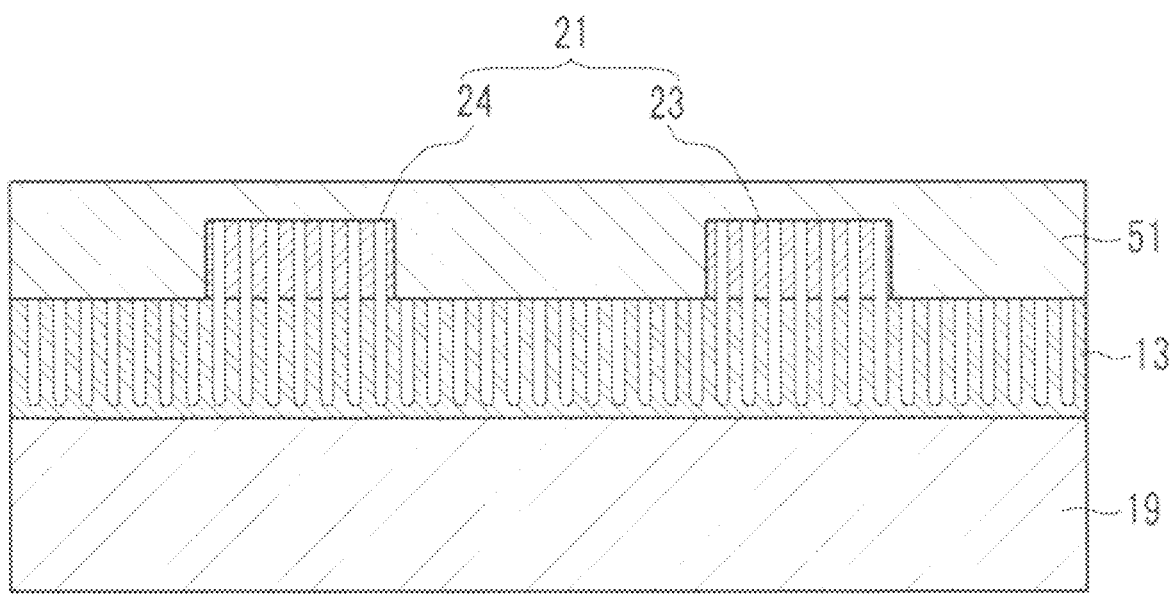
FIG. 10 is a cross-sectional view taken along the line X-X of FIG. 9.

FIG. 9 is a perspective view of a humidity sensor according to a sixth exemplary embodiment of the present invention, and FIG. 10 is a cross-sectional view taken along the line X-X of FIG. 9.

Referring to FIGS. 9 and 10, a humidity sensor 50 according to the exemplary embodiment includes a substrate 19, an anodic aluminum oxide (AAO) layer 13 formed on the substrate 19, electrodes 21 formed on the anodic aluminum oxide layer 13, and a polymer layer 51 covering the electrodes 21.

The humidity sensor according to the exemplary embodiment has the same structure as the humidity sensor according to the second exemplary embodiment except for the polymer layer 51. Therefore, the same elements will not be repetitively described.

The humidity sensor 50 according to the exemplary embodiment includes the electrodes 21 and the polymer layer 51 that are formed on the electrodes 21. The polymer layer 51 protects the electrodes 21 and the anodic aluminum oxide layer 13 from impurities such as dust, etc. As such, when the polymer layer 51 is formed, sensitivity and accuracy of the humidity sensor are prevented from being deteriorated by protecting the electrodes 21 and the anodic aluminum oxide layer 13 from the impurities to thereby extend the lifespan of the humidity sensor.

In the exemplary embodiment, although the electrodes 21 include a first electrode 23 and a second electrode 24 and electrode protrusions 23a and 24a formed in the first and second electrodes 23 and 24 and engaged with each other, the present invention is not limited thereto, and the electrodes may be formed in one plate shape as described in the third exemplary embodiment.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A humidity sensor comprising:
a substrate;
an anodic aluminum oxide layer formed on the substrate, having a plurality of holes formed therein and serving as a humidity sensing layer; and
electrodes formed on the anodic aluminum oxide layer.

2. The humidity sensor of claim 1, wherein
a plurality of holes are formed in the electrodes.

3. The humidity sensor of claim 2, wherein
the holes formed in the electrodes and the holes formed in the anodic aluminum oxide layer are in communication with each other.

4. The humidity sensor of claim 2, wherein
the electrodes have a thickness of 30 nm to 200 nm.

5. The humidity sensor of claim 1, wherein
the electrodes include a first electrode and a second electrode disposed adjacent to the first electrode.

6. The humidity sensor of claim 5, wherein
the first and second electrodes include electrode protrusions, and the electrode protrusions of the first electrode are fitted between the electrode protrusions of the second electrode.

7. The humidity sensor of claim 1, wherein
the electrodes are formed by one plate shape, the electrodes are electrically connected with the substrate, and a power supply is connected thereto.

8. The humidity sensor of claim 7, wherein
openings opened upward are formed in the electrodes.

9. The humidity sensor of claim 1, further comprising
a polymer layer protecting the electrodes,
wherein the electrodes are positioned between the polymer layer and the anodic aluminum oxide layer.

10. The humidity sensor of claim 1, further comprising
a heater connected with the anodic aluminum oxide layer.

11. The humidity sensor of claim 7, wherein
the power supply and a capacitance meter are connected to the electrodes.

12. A method of fabricating a humidity sensor, the method comprising:
preparing an aluminum substrate;
forming an anodic aluminum oxide layer by oxidizing the aluminum substrate; and
forming electrodes having holes formed on the anodic aluminum oxide layer,
wherein the anodic aluminum oxide layer serves as a humidity sensing layer.

13. The method of claim 12, further comprising patterning the electrodes.

14. The method of claim 13, wherein
patterning the electrodes includes forming a resist layer on the electrodes, exposing the resist layer, and etching the electrodes.

15. The method of claim 12, wherein
forming the electrodes includes evaporating a metal constituting the electrodes at a speed of 1 Å/s to 0.2 Å/s.

16. The method of claim 12, wherein
forming the electrodes includes evaporating a metal constituting the electrodes in a state in which a shadow mask is installed on the anodic aluminum oxide layer.

* * * * *